United States Patent
Abe et al.

(10) Patent No.: US 7,625,386 B2
(45) Date of Patent: Dec. 1, 2009

(54) MEDICAL SUTURING TOOL

(75) Inventors: Kazuhiro Abe, Fukuroi (JP); Shigeaki Funamura, Fukuroi (JP)

(73) Assignee: Covidien AG (CH)

( * ) Notice: Subject to any disclaimer, the term of this patent is extended or adjusted under 35 U.S.C. 154(b) by 71 days.

(21) Appl. No.: 10/598,561

(22) PCT Filed: Mar. 3, 2005

(86) PCT No.: PCT/EP2005/002180

§ 371 (c)(1),
(2), (4) Date: Jun. 6, 2007

(87) PCT Pub. No.: WO2005/094697

PCT Pub. Date: Oct. 13, 2005

(65) Prior Publication Data

US 2007/0293876 A1    Dec. 20, 2007

(30) Foreign Application Priority Data

Mar. 2, 2004    (JP) .............................. 2004-057758

(51) Int. Cl.
A61B 17/04    (2006.01)
(52) U.S. Cl. ...................................... 606/144; 606/145
(58) Field of Classification Search .......... 606/144–145
See application file for complete search history.

(56) References Cited

U.S. PATENT DOCUMENTS

| | | | |
|---|---|---|---|
| 2,012,776 A | | 8/1935 | Roeder |
| 4,935,027 A | * | 6/1990 | Yoon ........................... 606/146 |
| 5,037,433 A | * | 8/1991 | Wilk et al. ................... 606/139 |
| 5,123,914 A | | 6/1992 | Cope |
| 5,281,237 A | | 1/1994 | Gimpelson |
| 5,336,231 A | * | 8/1994 | Adair .......................... 606/148 |
| 5,364,410 A | | 11/1994 | Failla et al. |
| 5,391,182 A | | 2/1995 | Chin |
| 5,462,560 A | * | 10/1995 | Stevens ....................... 606/144 |
| 5,499,991 A | | 3/1996 | Garman |

(Continued)

FOREIGN PATENT DOCUMENTS

DE    2900265 A1    7/1980

(Continued)

OTHER PUBLICATIONS

International Search Report, PCT/EP2005/002180, dated Jul. 6, 2005, 2 pages.

*Primary Examiner*—Julian W Woo
*Assistant Examiner*—Son Dang

(57) ABSTRACT

A medical suturing tool 10 is composed of an insertion puncture needle 13 having an insertion hole 13a, a retrieval puncture needle 14 disposed in parallel with the insertion puncture needle 13, a lock part 15, and a surgical suture 16. A vertically elongated opening 18 is formed on the side surface of the insertion puncture needle 13, and an engaging groove 19 including a wide upper portion 19a and a narrow lower portion 19b on the side surface of the retrieval puncture needle 14 at a position slightly lower than the portion opposing to the vertically elongated opening 18. The lock part 15 is composed of a spherical portion 15a which can pass through a wide upper portion 18a and cannot pass through a narrow lower portion 18b and a rod-shaped portion 15b which can pass through the narrow lower portion 18b.

11 Claims, 14 Drawing Sheets

U.S. PATENT DOCUMENTS

| | | | |
|---|---|---|---|
| 5,531,699 | A | 7/1996 | Tomba et al. |
| 5,562,684 | A | 10/1996 | Kammerer |
| 5,653,716 | A | 8/1997 | Malo |
| 5,665,096 | A * | 9/1997 | Yoon ............... 606/139 |
| 5,681,333 | A | 10/1997 | Burkhart |
| 5,722,981 | A * | 3/1998 | Stevens ............ 606/148 |
| 5,782,845 | A * | 7/1998 | Shewchuk ......... 606/144 |
| 5,895,395 | A * | 4/1999 | Yeung .............. 606/144 |
| 5,897,563 | A * | 4/1999 | Yoon et al. ........ 606/144 |
| 5,921,993 | A * | 7/1999 | Yoon ............... 606/140 |
| 6,022,360 | A | 2/2000 | Reimels |
| 6,066,146 | A | 5/2000 | Carroll et al. |
| 6,110,183 | A | 8/2000 | Cope |
| 6,113,610 | A * | 9/2000 | Poncet ............. 606/139 |
| RE36,974 | E | 11/2000 | Bonutti |
| 6,451,024 | B1 | 9/2002 | Thompson et al. |
| 6,500,184 | B1 | 12/2002 | Chan et al. |
| 6,524,317 | B1 | 2/2003 | Ritchart |
| 6,638,286 | B1 * | 10/2003 | Burbank et al. ..... 606/157 |
| 6,699,263 | B2 | 3/2004 | Cope |
| 7,090,690 | B2 | 8/2006 | Foerster et al. |
| 7,320,693 | B2 * | 1/2008 | Pollack et al. ...... 606/144 |
| 2004/0039442 | A1 | 2/2004 | St. Goar et al. |
| 2004/0122473 | A1 | 6/2004 | Ewers et al. |
| 2004/0249395 | A1 | 12/2004 | Mikkaichi et al. |
| 2006/0069398 | A1 | 3/2006 | Suzuki et al. |
| 2007/0118153 | A1 | 5/2007 | Funamura et al. |
| 2007/0179509 | A1 | 8/2007 | Nagata et al. |
| 2007/0282351 | A1 | 12/2007 | Harada et al. |

FOREIGN PATENT DOCUMENTS

| | | |
|---|---|---|
| JP | 4226643 | 8/1992 |
| JP | 05-161655 A | 6/1993 |
| JP | 06-024533 B2 | 4/1994 |
| JP | 07-328020 | 12/1995 |
| JP | 3331215 B1 | 8/2003 |
| JP | 2006025932 | 2/2006 |
| JP | 2006025933 | 2/2006 |
| JP | 2006025934 | 2/2006 |
| WO | 95/22932 A1 | 8/1995 |
| WO | 2004006782 A1 | 1/2004 |
| WO | 2006037639 A1 | 4/2006 |
| WO | 2006082810 A1 | 8/2006 |

* cited by examiner

MEDICAL SUTURING TOOL

TECHNICAL FIELD

The present invention relates to a medical suturing tool for suturing a portion to be sutured in a patient's body.

BACKGROUND ART

A medical suturing tool is known for fixing a portion to be sutured in a patient's body, specifically skin and internal organs. In one example, intake of fluid food such as liquid diet or nutrient preparation is accomplished using a gastric fistula-forming tube when capability to take food orally is lowered as a result of advanced age or illness. To attach the gastric fistula-forming tube a hole on a belly of the patient is formed. In order to attach the gastric fistula-forming tube appropriately, the abdominal wall and stomach wall are fixed together in advance, using a medical suturing tool.

In JP-A-5-161655, a medical suturing tool is provided with two puncture needles provided in parallel at a distance and, when suturing, the two puncture needles simultaneously puncture a portion to be sutured of the patient. Subsequently, a surgical suture is passed through one of the puncture needles, and an inner needle having a loop member formed of wire connected to the distal end thereof is passed through the other puncture needle, and the inner needle is pulled out from the puncture needle in a state in which the surgical suture is engaged with the loop member. Then, the two puncture needles are pulled out from the patient, and both ends of the surgical suture projecting out from the patient's body are knotted together to complete suturing. The distal end of the puncture needle, which accommodates the inner needle inserted therein, is formed into a bent portion, and hence the distal opening is directed laterally, whereby the loop member projects outward so as to extend laterally to enable engagement of the surgical suture when the inner needle is pushed into the puncture needle.

DISCLOSURE OF THE INVENTION

However, with the medical suturing tool described above, it is necessary to insert the inner needle or the surgical suture through both of the puncture needles, and hence there arises a problem such that the operation becomes complicated. When insertion of the inner needle into the puncture needle is not performed well, the direction of projection or the shape of the loop member may be incorrect, so that there may be the case in which the surgical suture cannot be engaged. In the case in which a space inside the portion to be sutured is not large enough, it is difficult to cause the surgical suture to engage with the loop member, and hence there arises a problem that the likelihood of success is too low. Furthermore, the pair of the puncture needles are formed of thin-walled cylindrical hollow needle to allow the surgical suture or the inner needle to pass therethrough, whereby the rigidity is low. Consequently, there arises a problem that there may be the case in which the puncture needle is distorted during the puncturing step, so that it cannot then be accurately inserted to a desired location.

In order to cope with such problems, it is an object of the present invention to provide a medical suturing tool which ensures appropriate suturing with a simple operation.

In order to achieve the above-described object, a medical suturing tool according to the present invention is structurally characterized by comprising: an insertion puncture needle formed with an insertion hole from the proximal end to the distal end; a retrieval puncture needle disposed substantially in parallel with the insertion puncture needle at a predetermined distance therefrom; and a surgical suture extending from the proximal end to the distal end of the insertion puncture needle and then engaged with the distal end of the retrieval puncture needle via an engaging portion.

In the medical suturing tool according to the present invention configured as described above, a skin-side layer and the portion to be sutured of the patient can be fixed by inserting the insertion puncture needle and the retrieval puncture needle from the side of the skin surface of the patient into the portion to be sutured while keeping a predetermined distance, pulling out the insertion puncture needle and the retrieval insertion puncture needle from the skin surface of the patient in a state in which the distal end of the surgical suture is passed through the insertion puncture needle from the proximal end to the distal end and then is engaged with the distal end of the retrieval puncture needle via the engaging portion, and knotting the both end portions of the surgical suture located outside the patient's body.

In other words, by engaging the distal end of the surgical suture passed through the insertion puncture needle with the retrieval puncture needle via the engaging portion, the surgical suture and the retrieval puncture needle can form a loop which surrounds the tissue to be sutured. Therefore, by pulling out the insertion puncture needle and the retrieval puncture needle in this state, both end portions of the surgical suture extend outside the patient's body, so that suturing can be completed by knotting together the end portions. Therefore, the suturing operation is facilitated. In this case, the engaging portion for allowing the surgical suture to engage with the retrieval puncture needle may be formed by providing a recess or a projection for engagement on the retrieval puncture needle, or by other engaging members.

The medical suturing tool according to the present invention is structurally characterized by comprising: an elongate opening provided on a surface of the insertion puncture needle facing the retrieval puncture needle in communication with the insertion hole; an engaging member being capable of moving in the insertion hole of the insertion puncture needle and, when having reached a predetermined position in the insertion hole, bending from the side of the upper end portion thereof to project outside through the elongate opening; and an engaging groove provided on a surface of the retrieval puncture needle opposing to the insertion puncture needle, and in that the surgical suture is connected to the lower end of the engaging member so that the suturing tool engages with the engaging groove on the retrieval puncture needle after having passed from the proximal end to the distal end of the insertion puncture needle together with the engaging member.

In the medical suturing tool according to the present invention configured as described above, the engaging member is provided within the insertion hole of the insertion puncture needle in a movable state, and the engaging member is adapted to be bent outward from the elongate opening provided on the side surface of the insertion puncture needle when the engaging member reaches the predetermined position. The engaging groove is provided on the side surface of the retrieval puncture needle, so that the engaging member being bent and projecting from the insertion puncture needle can be stored in a storage recess in a state of being engaged.

In other words, the engaging member inserted from the proximal end into the insertion hole of the insertion puncture needle is bent from the side of the upper end portion to the retrieval puncture needle when it reaches the position of the elongate opening and enters into the engaging groove, then the lower side portion of the engaging member is moved from the insertion puncture needle to the retrieval puncture needle side and stored in the storage recess. Since the surgical suture is connected to the lower end of the engaging member, the surgical suture passes from the proximal end of the insertion puncture needle through the elongate opening on the distal side, and then engages with the engaging groove on the distal side of the retrieval puncture needle via the engaging member.

In this case, it is preferable to perform the operation to pull the engaging member up to the position of the elongate opening by placing the distal portion (lower portion) of the surgical suture together with the engaging member within the insertion puncture needle at a position distally of the elongate opening once, and then pulling the surgical suture toward the proximal portion of the insertion puncture needle. Accordingly, the engaging member is bent toward the retrieval puncture needle while moving as if it rotates about the distal portion of the surgical suture. And when the upper end portion of the bent engaging member engages the engaging groove, the surgical suture is loosened and fed into the insertion puncture needle in sequence. Accordingly, the engaging member is thereafter accommodated in the engaging groove.

In this way both end portions of the surgical suture are outside the patient's body following puncturing with the insertion puncture needle and the retrieval puncture needle advancing into the portion to be sutured from the side of the skin surface of the patient in a state in which the engaging member including the surgical suture connected to the lower end is inserted into the insertion hole of the insertion puncture needle, and pulling the insertion puncture needle and the retrieval puncture needle out in a state in which the engaging member is engaged with the engaging groove of the retrieval puncture needle together with the surgical suture. Then, by knotting together the end portions of the surgical suture, suture is completed. In this case, the weight of the upper end portion of the engaging member may be increased so that the engaging member engages with the engaging groove under the gravitational fall of its own weight, to enter into the engaging groove with the upper end portion oriented downward, or the engaging member is adapted to rotate about the upper end portion thereof to enter into the engaging groove.

In the medical suturing tool according to the present invention the engaging groove includes a storage recess capable of accommodating the engaging member and an engaged portion with which the upper end portion of the engaging member can engage.

As described above, in the medical suturing tool of the present invention, since the engaging groove provided on the side surface of the retrieval puncture needle includes the storage recess capable of accommodating the engaging member, and the engaged portion with which the upper end portion of the engaging member, the engaging member inclined from and projecting from the insertion puncture needle can be stored in the storage recess in a state in which the upper end portion is engaged with the engaged portion. In other words, the engaging member inclined from the elongate opening of the insertion puncture needle entered at the upper end portion into the engaging groove rotates about the engaged portion in a state in which the upper end portion is engaged with the engaged portion, and the lower side portion of the engaging member is moved from the insertion puncture needle toward the retrieval puncture needle and stored into the storage recess.

The medical suturing tool according to the present invention may be further structurally characterized if the upper end portion of the engaging member is thicker than the lower side portion of the engaging member, the elongate opening of the insertion puncture needle including a relatively wide upper portion through which the upper end portion of the engaging member can pass and a narrower lower portion through which the upper end portion of the engaging member cannot pass and the lower side portion of the engaging member can pass, and the engaging groove of the retrieval puncture needle includes a relatively wide upper portion through which the upper end portion of the engaging member can pass and a narrower lower portion through which the upper end portion of the engaging member cannot pass but the lower side portion can pass.

In this arrangement, extension of the engaging member from the insertion puncture needle, and docking in the retrieval puncture needle can be performed smoothly in a simple structure, and the reliability of engagement of the surgical suture with the retrieval puncture needle increases. In this case, the upper end portion of the engaging member may be formed of a spherical body and the lower side portion of the engaging member may be formed of a rod member having smaller diameter than the spherical body. In this arrangement, taking over of the engaging member from the insertion puncture needle to the retrieval puncture needle can be performed smoothly.

The medical suturing tool according to the present invention may be further structurally characterized if an engaging wall is provided at the lower portion of the surface of the wide upper portion of the engaging groove of the retrieval puncture needle so that the upper end portion of the engaging member is prevented from coming off toward the outside from the wide upper portion of the engaging groove. Accordingly, since the upper end portion of the engaging member which enters into the engaging groove and is engaged with the engaged portion once is prevented from coming off from the engaging groove by the engaging wall, the surgical suture engages positively with the retrieval puncture needle via the engaging member.

The medical tutoring tool according to the present invention may be further structurally characterized if the portion on the distal side of the insertion puncture needle with respect to the elongate opening and at least part of the retrieval puncture needle other than the portion where the engaging groove is formed is formed as a solid portion. In this arrangement, the thin hollow portion formed in the insertion puncture needle and in the retrieval puncture needle can be minimized, whereby the rigidity of the insertion puncture needle and the retrieval puncture needle can be increased. Accordingly, the insertion puncture needle and the retrieval puncture needle can be inserted to an appropriate position of the patient. In this case, the shape of the insertion puncture needle and the retrieval puncture needle in lateral cross section is not limited to a circular shape, and may assume other shapes such as square or triangle. It is preferable to employ a shape which can increase the rigidity such as the square shape.

The medical suturing tool according to the present invention may be further structurally characterized if at least a portion of the insertion puncture needle where the elongate opening is formed and of at least a portion of the retrieval puncture needle where the engaging groove is formed are formed into an angular C-shape in lateral cross section, respectively, and are arranged so that the open sides are facing each other.

In this arrangement, the direction in which the engaging portion is inclined and projects from the insertion puncture needle become constant. Also, the engaging groove of the retrieval puncture needle which receives the engaging member projecting from the insertion puncture needle is also oriented to the front of the engaging member. Therefore, taking over of the engaging member from the insertion puncture needle to the retrieval puncture needle is ensured. In this case, the portion formed into the angular C-shape in lateral cross section may constitute the entirety of the insertion puncture needle and the retrieval puncture needle, or just a part. However, it is present at least at the elongate opening and the engaging groove. In this manner, by forming the lateral cross section into the angular C-shape, the rigidity of the insertion puncture needle and the retrieval puncture needle is increased, whereby the insertion puncture needle and the retrieval puncture needle are less inclined to bow or sag when under the stress of puncturing bodily tissue.

The medical suturing tool of the present invention may be further structurally characterized if needle points of the insertion puncture needle and the retrieval puncture needle are formed into a pointed conical shape or a tapered thin blade shape. When there is no opening at the needle points of the insertion puncture needle and the retrieval puncture needle, the shape of the needle points can be determined freely. For example, the tapered thin blade shape includes a shape like a cutting blade of the knife, or a thin-plate shape whereof one of the edges is perpendicular and the other edge is inclined. By forming the needle points in these shapes, puncture of the insertion puncture needle and the retrieval puncture needle can be performed smoothly.

The medical suturing tool according to the present invention can be further structurally characterized if at least one of the insertion puncture needle and the retrieval puncture needle is formed by the combination of a metal component and a resin component. In this case, for example, the portion of the insertion puncture needle where the elongate opening is provided and the portion of the retrieval puncture needle where the engaging groove is provided may be constituted of members formed of resin material, and the remaining portions are constituted of members formed of metal material. In this arrangement, formation of the elongate opening or the engaging groove may be facilitated, and the rigidity of other portions can be improved, thereby enhancing strength thereof.

The medical suturing tool according to the present invention may be further structurally characterized if the insertion puncture needle and the retrieval puncture needle are attached to a retaining member. In this arrangement, the retaining member can position the insertion puncture needle and the retrieval puncture needle at functional relative positions, and hence puncturing operation into the portion to be sutured of the patient is facilitated. In this case, the insertion puncture needle and the retrieval puncture needle can be detachably mounted to the retaining member. In this arrangement, since the insertion puncture needle and the retrieval puncture needle are attachable and detachable with respect to the retaining member, the medical suturing tool can be used a plurality of times only by freely changing one or other of the puncture needles, according to the situation.

For example, it is a consequence of preparing a plurality of cartridges having the engaging member and the surgical suture pushed into the insertion puncture needle that, when the operation is to be repeated for a plurality of times, this can be done only by replacing an entire cartridge. In this way, the troublesome operation of inserting the engaging member or the surgical suture into the insertion puncture needle every time can be avoided. The method of attachment and detachment may employ a mechanism such that a hole or the like is formed on a plate-shaped retaining member and the insertion puncture needle and the retrieval puncture needle are inserted or pulled out to/from this hole, or a mechanism such that a notch is formed on the retaining member and the insertion puncture needle and the retrieval puncture needle are attached or detached to/from the notch.

The medical suturing tool according to the present invention may be further structurally characterized if the retaining member is constituted of a grip member for holding by hand. In this arrangement, since the retaining member for retaining the insertion puncture needle and the retrieval puncture needle can be used as the grip member for holding by hand, it is not necessary to provide an additional grip member, whereby the number of parts for constituting the medical suturing tool can be reduced. It is preferable to increase the length of a part of the retaining member which holds the insertion puncture needle and the retrieval puncture needle. In this arrangement, the medical suturing tool can easily be held by hand and hence the operation is facilitated and the insertion puncture needle and the retrieval puncture needle can be strongly retained.

The medical suturing tool according to the present invention may be further structurally characterized if a positioning member for regulating the mounting positions of the insertion puncture needle and the retrieval puncture needle with respect to the retaining member is provided. The positioning member in this case includes the one which effects positioning in the direction about the axis with respect to the insertion puncture needle and the retrieval puncture needle, and the one which effects positioning in the axial direction. The positioning member for the direction about the axis may be those having structures such that the insertion puncture needle and the retrieval puncture needle are polygonal in lateral cross section and are formed with a projection or a recess on the side surfaces thereof, while the retaining member is formed with retaining holes of polygonal shape and are formed with a recess or a projection on the inner peripheral surface of the retaining hole so as to be fitted with the projection or the recess.

On the other hand, the positioning member in the axial direction may be a structure such that a projection or a shoulder is provided on the insertion puncture needle and the retrieval puncture needle, and the retaining member is provided with a groove which can be engaged with the projection or the shoulder. Accordingly, the insertion puncture needle and the retrieval puncture needle can be attached to the retaining member so as to be at the constant relative position, whereby enabling more consistent suturing.

The medical suturing tool according to the present invention may be further structurally characterized if a plurality of pairs of the insertion puncture needle and the retrieval puncture needle are provided on the retaining member. When suturing the target tissue, it can be that there is a plurality of locations to be sutured, rather than just one location. In such a case, when the required number of the insertion puncture needles and the retrieval puncture needles are mounted to the retaining member, suturing can be performed in one operation at all the locations so that suturing can be performed effectively in a shorter time.

BEST MODE FOR CARRYING OUT THE INVENTION

First Embodiment

Figure 1:
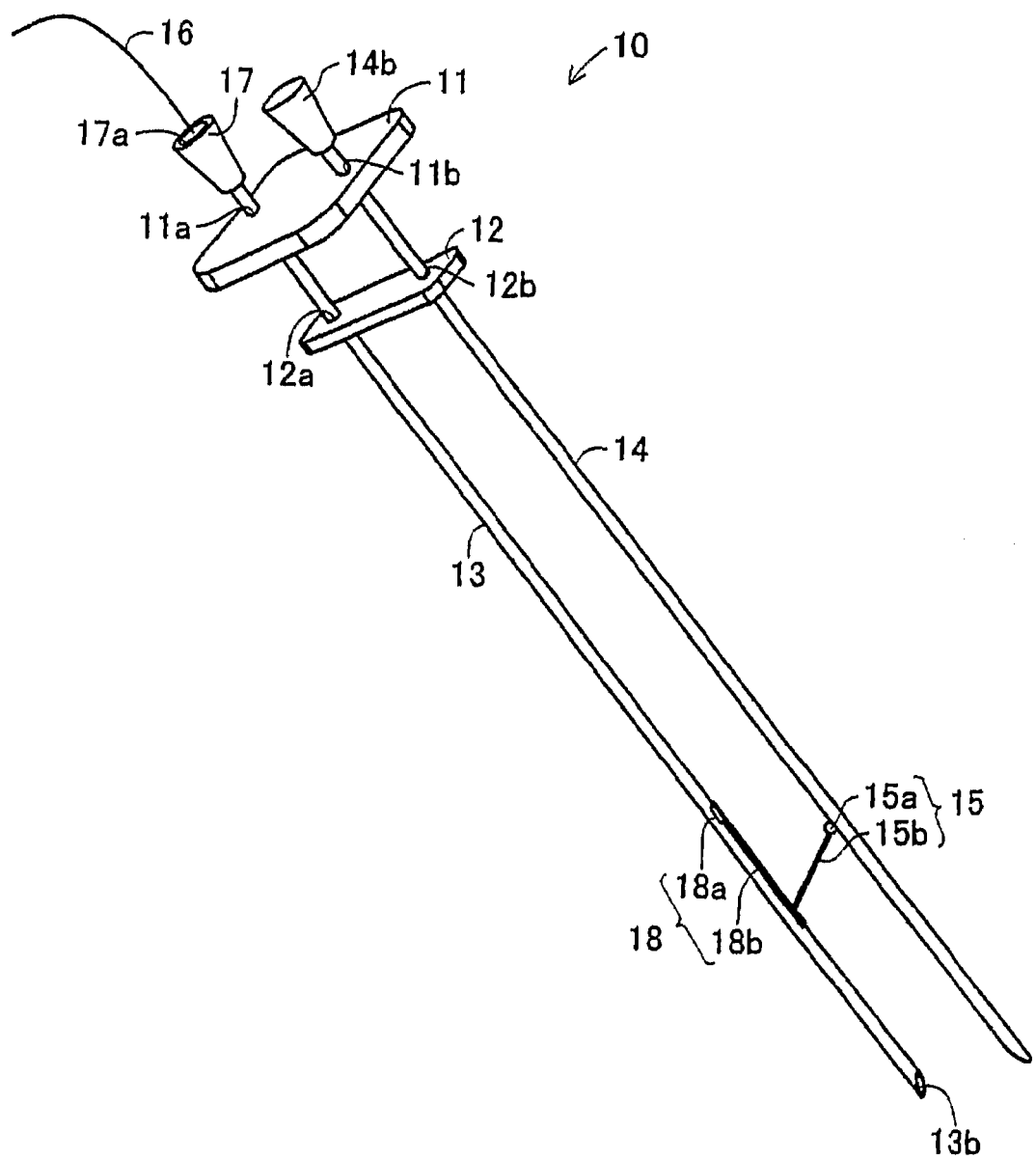
FIG. 1 is a perspective view of a medical suturing tool according to a first embodiment of the present invention.
Figure 2:
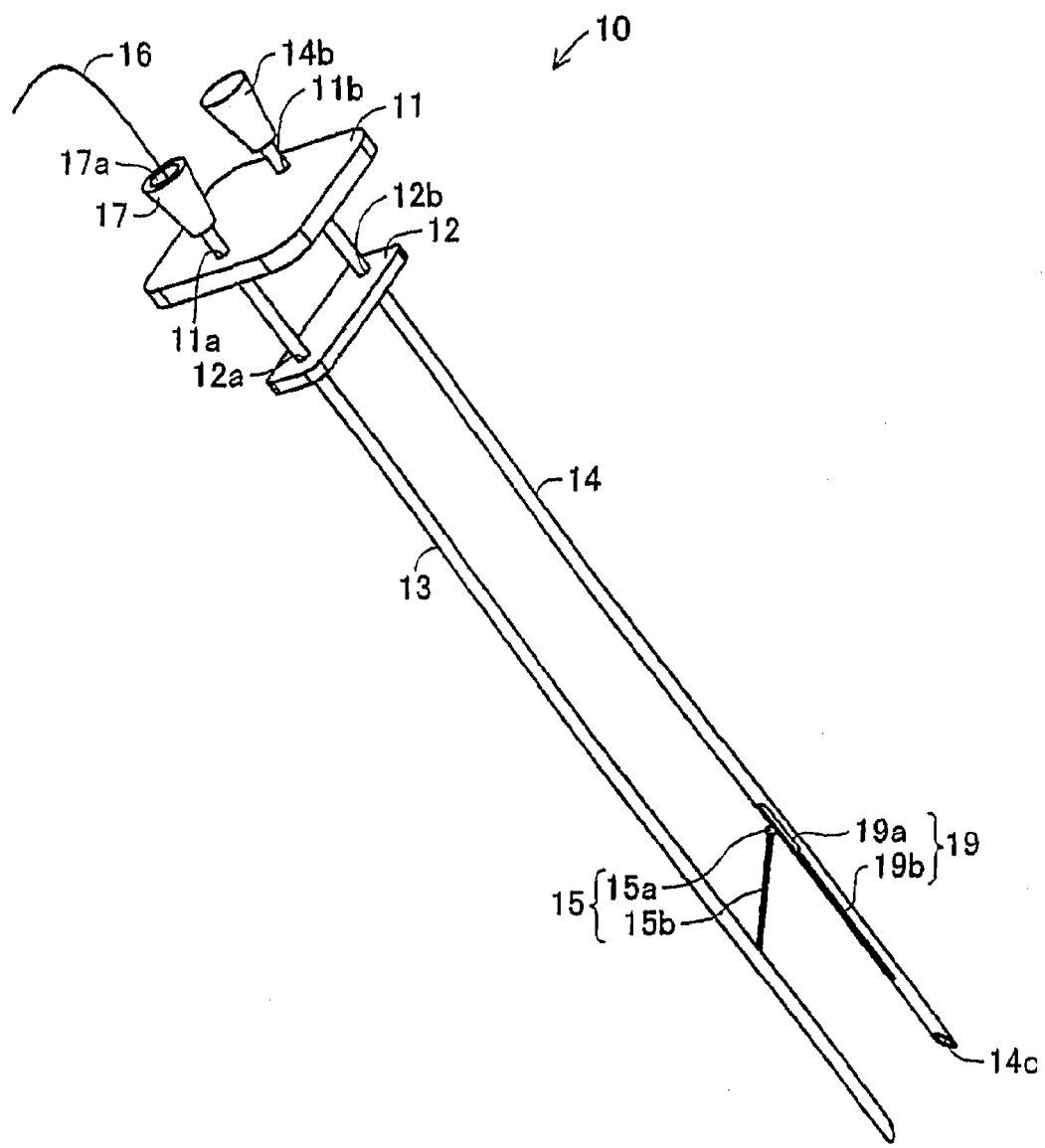
FIG. 2 is a perspective view of the medical suturing tool shown in FIG. 1 viewed from another direction.
Figure 3:
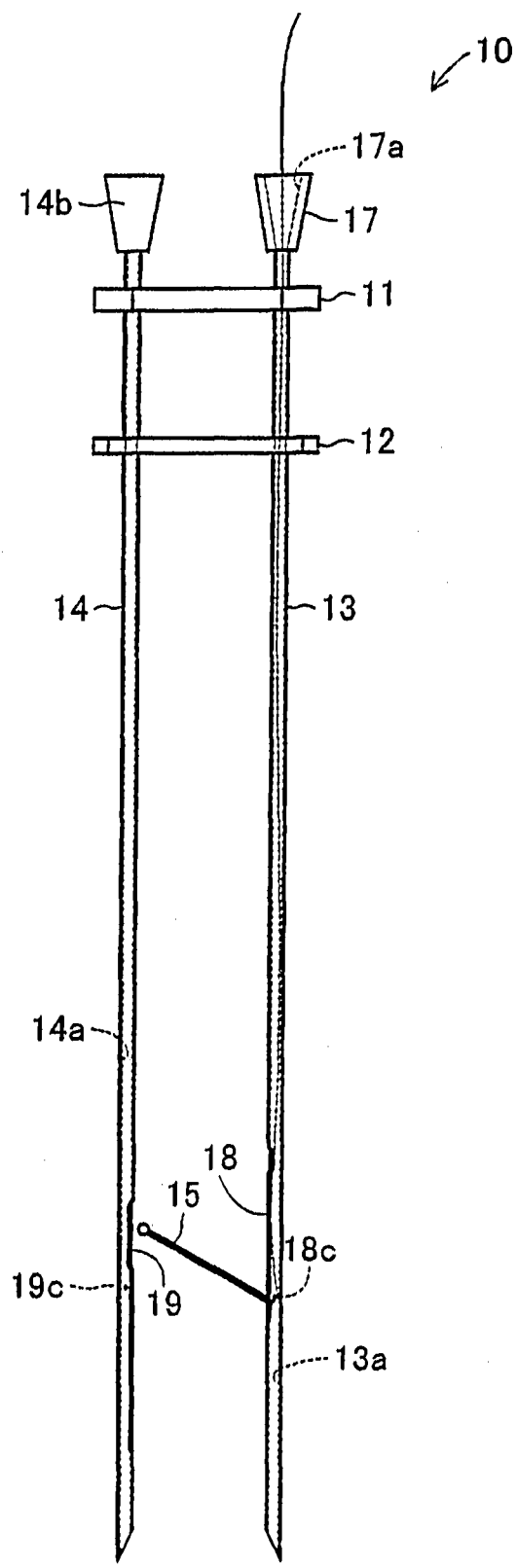
FIG. 3 is a front view of the medical suturing tool shown in FIG. 1 and FIG. 2.

Referring to the drawings, a first embodiment of the present invention will be described. FIG. 1 to FIG. 3 shows a medical suturing tool 10 according to the first embodiment. The medical suturing tool 10 includes an upper retaining member 11 and a lower retaining member 12 which constitute the retaining member of the present invention, a pair of puncture needles including an insertion puncture needle 13 and a retrieval puncture needle 14 to be detachably attached to the upper retaining member 11 and the lower retaining member 12, and a lock part 15 as an engaging member in the present invention, and a surgical suture 16.

The upper retaining member 11 and the lower retaining member 12 are formed of mold of resin material. The upper retaining member 11 is formed into a substantially square plate shape with the corners cut and rounded into curved shape, and the lower retaining member 12 is formed into a substantially rectangular plate shape with the corners cut and rounded into curved shape. Then, both side portions of the retaining member 11 is formed with circular retaining holes 11a, 11b at a constant distance with the intermediary of a center point of the upper retaining member 11, and both side portions of the lower retaining member 12 along the longitudinal direction are formed with circular retaining holes 12a, 12b at the same distance as that between the retaining holes 11a, 11b.

The insertion puncture needle 13 is formed of a metal cylindrical member provided with an insertion hole 13a therein, and is provided with a grip member 17 at the proximal end (upper end) thereof. The grip member 17 is formed into a cylindrical shape including an upper side being large in diameter, and a lower side being small in diameter, and is formed inside with a guide hole 17a which communicates with the insertion hole 13a. The guide hole 17a includes the upper side being large in diameter and the lower side being small in diameter so as to be analogous with the outer peripheral surface of the grip member 17. Accordingly, the lock part 15 and the surgical suture 16 can easily be inserted into the insertion hole 13a of the insertion puncture needle 13 from above the grip member 17.

Figure 4:
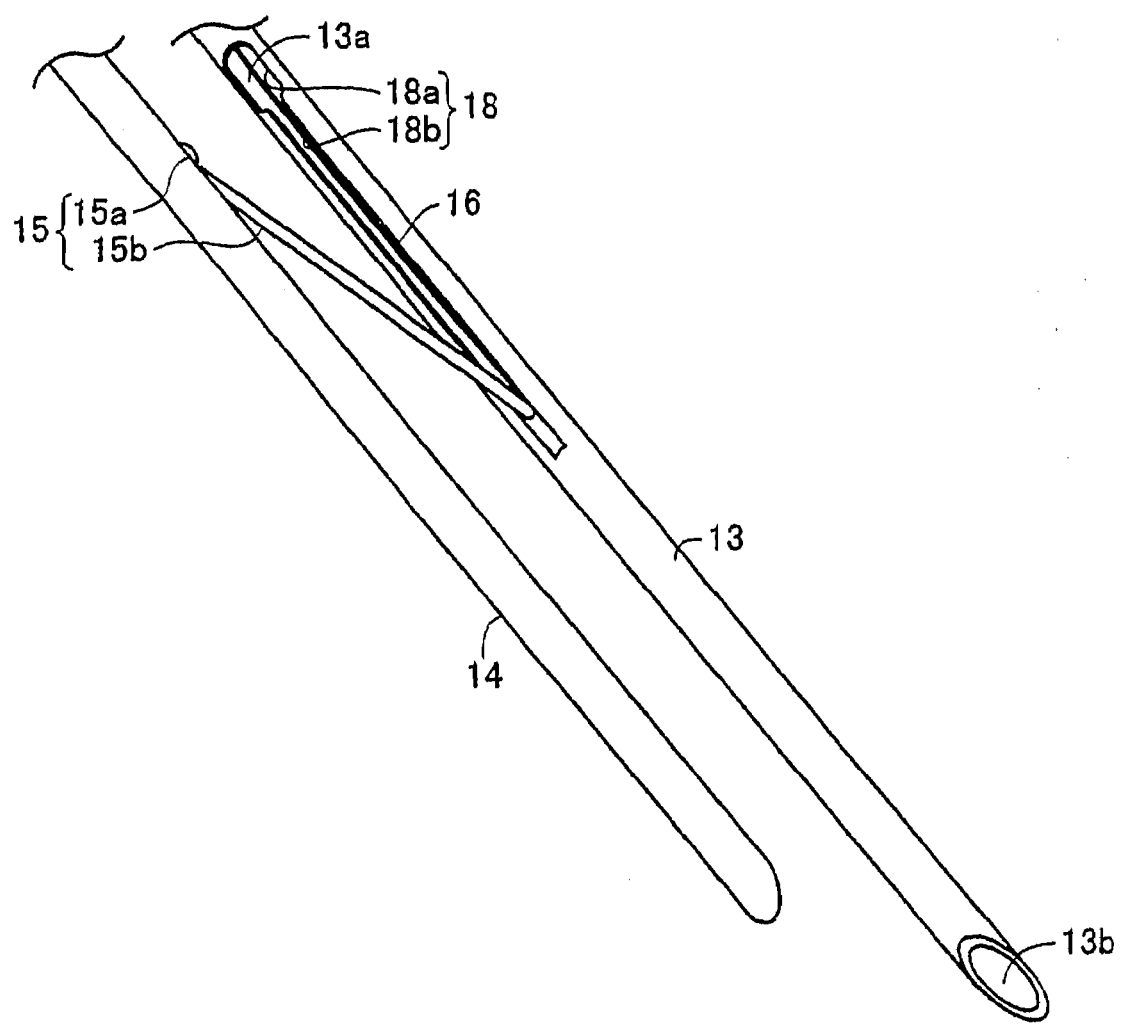
FIG. 4 is a perspective view showing an elongate opening provided on the medical suturing tool.
Figure 5:
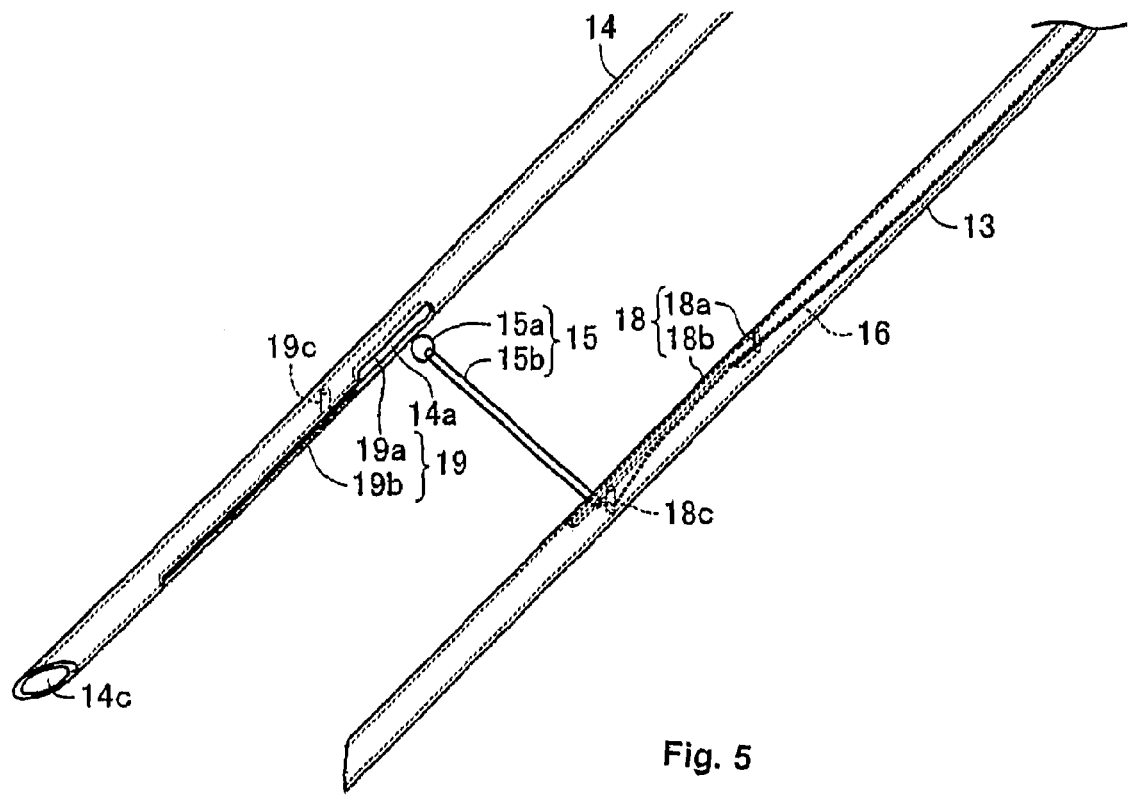
FIG. 5 is a perspective view showing a rotation base and an engaged portion.

The distal end portion (lower end portion) of the insertion puncture needle 13 is cut obliquely so that an opening 13b can be seen from the side. The insertion puncture needle 13 is formed with a vertically elongated opening 18 on the lower portion of the peripheral surface where the upper end portion of the opening 13b is located, as shown in FIG. 4. The upper end of the vertically elongated opening 18 is configured of a wide upper portion 18a having a wider width and a shorter length, and the lower end thereof is configured of a narrow lower portion 18b having a narrow width and a longer length. As shown in FIG. 5, a rotation base 18c is provided in the insertion puncture needle 13 at the position in the vicinity of the lower end of the narrow lower portion 18b. The rotation base 18c is formed of a rod member and extends across the inner surface of the insertion puncture needle 13.

The insertion puncture needle 13 is retained in a state of being inserted into the retaining hole 11a of the upper retaining member 11 and the retaining hole 12a of the lower retaining member 12 with the opening 13b and the vertically elongated opening 18 faced toward the center of the upper retaining member 11 and the lower retaining member 12. The upper retaining member 11 retains the insertion puncture needle 13 at the position near the proximal portion, and the lower retaining member 12 retains the portion of the insertion puncture needle 13 on the lower side portion with respect to the proximal portion at a distance apart from the upper retaining member 11. The mounting position of the lower retaining member 12 with respect to the insertion puncture needle 13 in this case is to be set as needed according to the projecting amount of the portion lower than the lower retaining member 12 of the insertion puncture needle 13.

Figure 6:
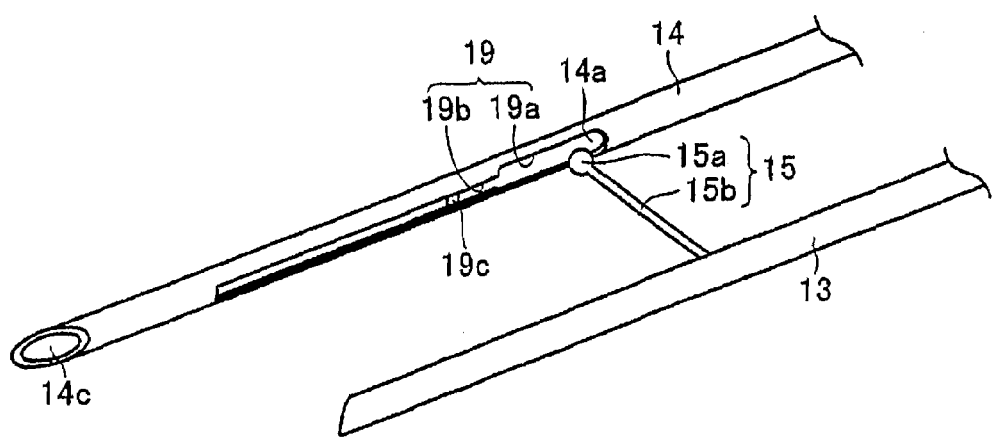
FIG. 6 is a perspective view showing an engaging groove provided on the medical suturing tool.

The retrieval puncture needle 14 is formed of a metal cylindrical member formed with a hole 14a therein in the same manner as the insertion puncture needle 13, and is provided with a grip member 14b at the proximal end thereof. The grip member 14b is formed into a column shape having an upper side being large in diameter and a lower side being small in diameter, and is not formed with a guide hole. The distal end of the retrieval puncture needle 14 is cut obliquely and formed with an opening 14c so as to be viewed from the side. At a lower position of the peripheral surface of the retrieval puncture needle 14 where the upper end portion of the opening 14c is located, there is formed with an engaging groove 19 as shown in FIG. 6.

The upper side portion of the engaging groove 19 is configured of a wide upper end portion 19a having a wider width and a shorter length, and the lower end portion thereof is configured of a narrow lower portion 19b having a narrow width and a longer length. An engaged portion 19c for reducing the hole diameter of the hole 14a is formed at a position in the hole 14a slightly lower than the upper end of the narrow lower portion 19b. The engaged portion 19c is formed of a rod member, and is extended across the inner surface of the retrieval puncture needle 14. Therefore, the engaging wall of the present invention is defined between the lower end of the wide upper portion 19a and the engaged portion 19c of the edge of the engaging groove 19.

The retrieval puncture needle 14 is inserted into and retained by the retaining hole 11b of the upper retaining member 11 and the retaining hole 12b of the lower retaining member 12 in a state in which the opening 14c and the engaging groove 19 faced toward the insertion puncture needle 13. The upper retaining member 11 and the lower retaining member 12 retain the retrieval puncture needle 14 in parallel with the insertion puncture needle 13. In this case, the retrieval puncture needle 14 is retained by the upper retaining member 11 and the lower retaining member 12 in such a manner that the upper end of the engaging groove 19 is positioned slightly upper than the lower end of the vertically elongated opening 18.

The lock part 15 includes a spherical portion 15a formed of metal material and a cylindrical rod-shaped portion 15b connected to the spherical portion 15a, and the diameter of the spherical portion 15a is set to be larger than the diameter of the rod-shaped portion 15b. The length of the lock part 15 is set to a length which can be bridged between the insertion puncture needle 13 and the retrieval puncture needle 14 orthogonally, the diameter of the lock part 15 (the diameter of the spherical portion 15a) is set to a size which can move within the insertion hole 13a of the insertion puncture needle 13.

The diameter of the spherical portion 15a is set to a size which can pass through the wide upper portion 18a of the vertically elongated opening 18 and the wide upper portion 19a of the engaging groove 19, and cannot pass through the narrow lower portion 18b of the vertically elongated opening 18 and the narrow lower portion 19b of the engaging groove 19. The diameter of the rod-shaped portion 15b is set to a size which can pass through entire portion of the vertically elongated opening 18 and the engaging groove 19. The diameter of the spherical portion 15a is set to a size that when the lock part 15 is entered into the hole 13a, the spherical portion 15a engages with a rotation base 18c and hence cannot move further downward, and when the lock part 15 is entered into the hole 14a, the spherical portion 15a engages the engaged portion 19c and hence cannot move further downward. The length of the vertical direction of the vertically elongated opening 18 and the engaging groove 19 are set to a length longer than the lock part 15.

Figure 7:
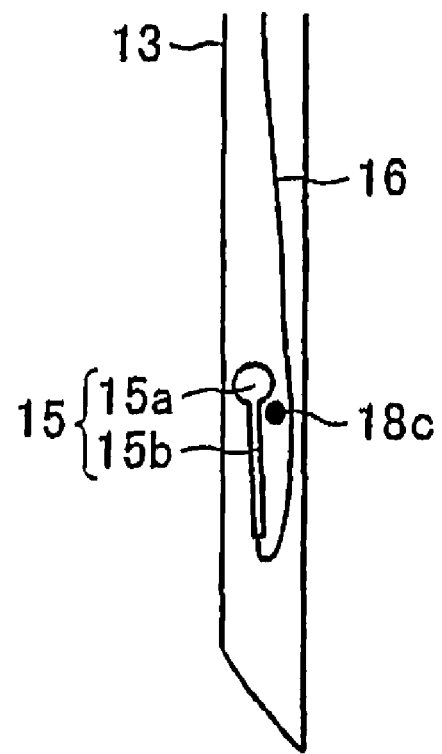
FIG. 7 is a cross-sectional view showing a state in which a lock part is attached into an insertion puncture needle.

Then, a distal end of the surgical suture 16 is connected to an end (the lower end in the initial state to be accommodated in the insertion puncture needle 13) of the rod-shaped portion 15b of the lock part 15. The lock part 15 is inserted into the guide hole 17a of the grip member 17 from the side of the end of the rod-shaped portion 15b together with the surgical suture 16, and accommodated in the insertion hole 13a of the insertion puncture needle 13. In this case, it is adapted in such a manner that the spherical portion 15a of the lock part 15 is positioned on the lower side (on the distal side of the insertion puncture needle 13) than the wide upper portion 18a of the vertically elongated opening 18 by feeding the surgical suture 16 into the insertion puncture needle 13 in sequence. In this case, as shown in FIG. 7, it is adapted in such a manner that the spherical portion 15a engages with the rotation base 18c, and the rotation base 18c is located between the lock part 15 and the surgical suture 16.

Figure 8:
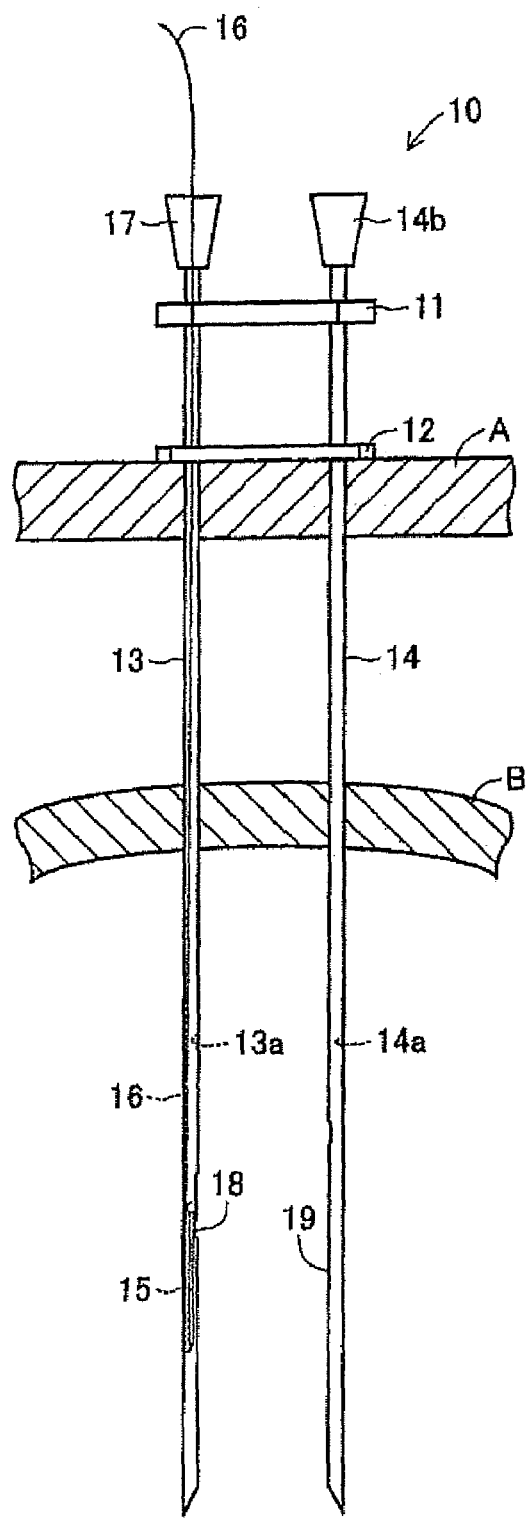
FIG. 8 is a cross-sectional view showing a state in which the medical suturing tool is punctured into an abdominal portion.

In this structure, for example, when the abdominal wall and the stomach wall of the patient are sutured using the medical suturing tool 10, the medical suturing tool 10 is pushed into the surface of the skin at the abdominal part of the patient first as shown in FIG. 8, and then the insertion puncture needle 13 and the retrieval puncture needle 14 are punctured into an abdominal wall A and a stomach wall B. In this case, the insertion puncture needle 13 and the retrieval puncture needle 14 are advanced through the respective punctures until the lower retaining member 12 comes into abutment with the skin surface, so that the vertically elongated opening 18 and the engaging groove 19 are located inside the stomach wall B.

Figure 9:
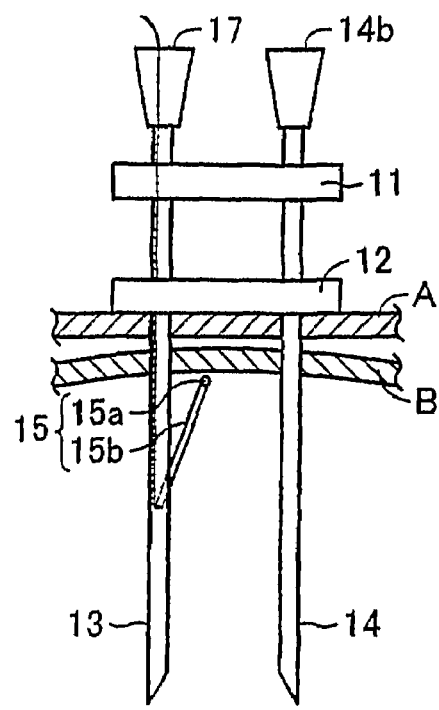
FIG. 9 is a cross-sectional view showing a state in which the lock part is projecting from the insertion puncture needle.
Figure 10:
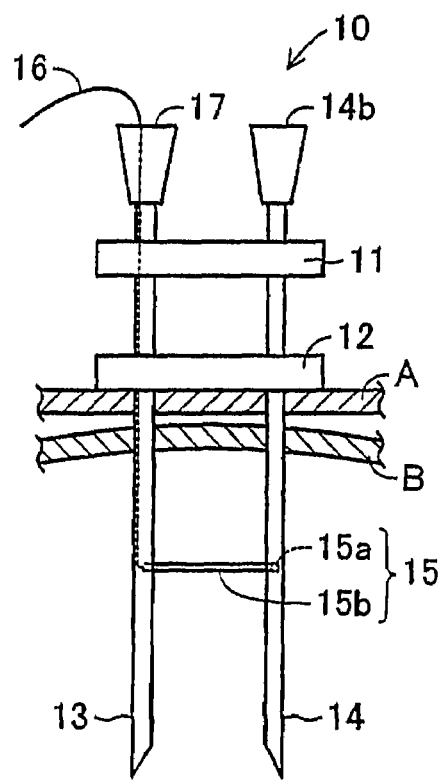
FIG. 10 is a cross-sectional view showing a state in which the lock part projecting from the insertion puncture needle is extended across in a retrieval puncture needle.

Subsequently, the surgical suture 16 is pulled to lift the lock part 15 toward the proximal portion of the insertion puncture needle 13. With this operation, when the spherical portion 15a of the lock part 15 reaches the wide upper portion 18a of the vertically elongated opening 18, that is, when the lower end of the lock part 15 reaches the rotation base 18c, the lock part 15 starts rotating about the rotation base 18c. Consequently, as shown in FIG. 9, the spherical portion 15a passes through the wide upper portion 18a and the rod-shaped portion 15b passes through the narrow lower portion 18b, so that the lock part 15 is bent toward the retrieval puncture needle 14. Then, when the lock part 15 is bent to almost horizontal state, the spherical portion 15a passes through the wide upper portion 19a of the engaging groove 19 and enters the hole 14a. The spherical portion 15a entered the hole 14a is lowered to the position of the engaged portion 19c, whereby the lock part 15 takes a substantially horizontal state as shown in FIG. 10.

Figure 11:
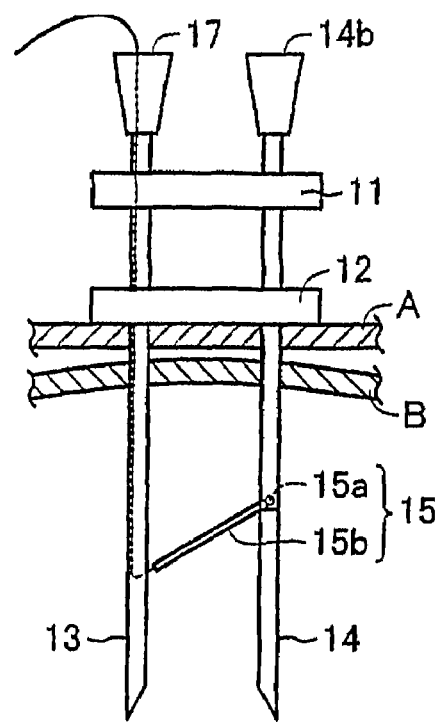
FIG. 11 is a cross-sectional view showing a state in which the lock part is taken over to the retrieval puncture needle.
Figure 12:
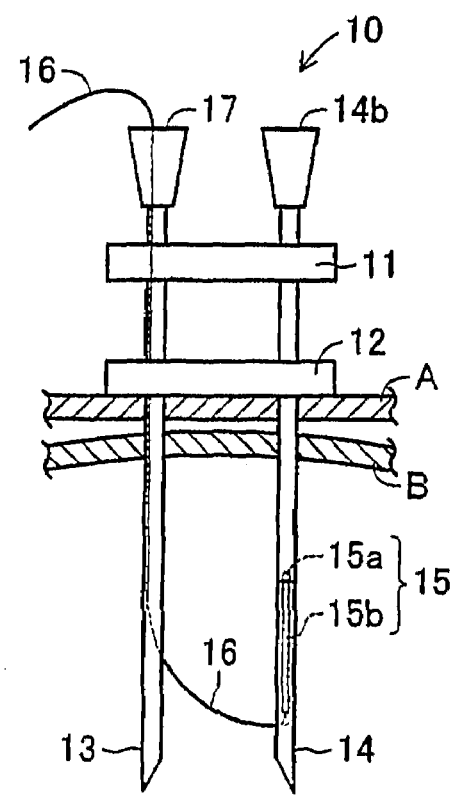
FIG. 12 is a cross-sectional view showing a state in which the lock part is accommodated in the retrieval puncture needle.

Subsequently, when the surgical suture 16 is loosened, the surgical suture 16 is pulled into the insertion puncture needle 13 by a predetermined length due to the weight of the lock part 15. Accordingly, the lock part 15 rotates about the spherical portion 15a, and, as shown in FIG. 11, the rod-shaped portion 15b of the lock part 15 moves out from the insertion puncture needle 13. Then, when the surgical suture 16 is further fed into the insertion puncture needle 13, the rod-shaped portion 15b passes through the narrow lower portion 19b and the lock part 15 is stored in the hole 14a as shown in FIG. 12.

Figure 13:
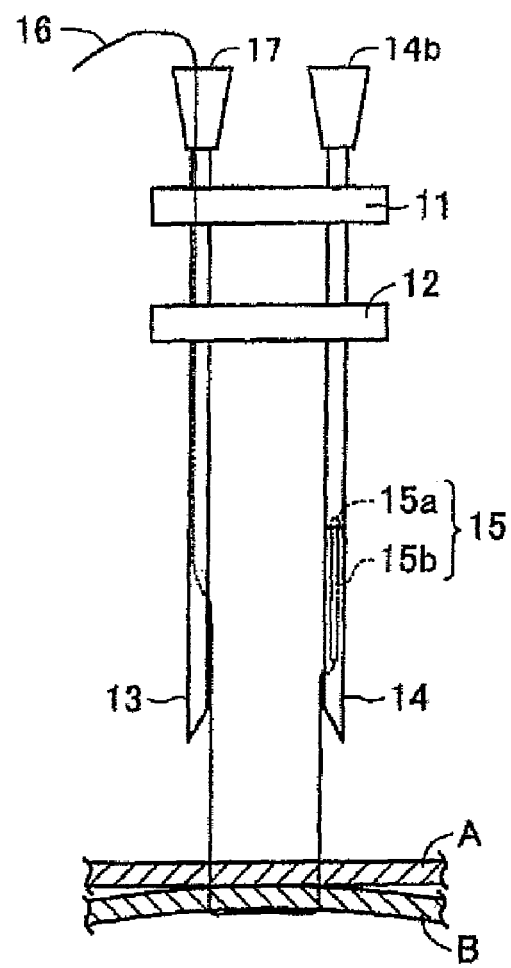
FIG. 13 is a cross-sectional view showing a state in which an abdominal wall and a stomach wall are joined by a surgical suture.
Figure 14:
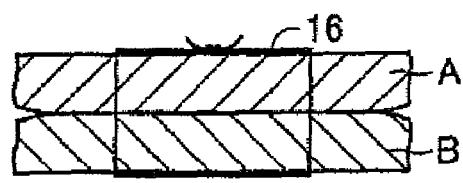
FIG. 14 is a cross-sectional view showing a state in which suturing is completed.

In this state, the medical suturing tool 10 is pulled and removed out from the patient's body. In this case, the lock part 15 is brought into a state of being fixed in the retrieval puncture needle 14 by the engagement between the spherical portion 15a and the engaged portion 19c, and the surgical suture 16 is brought into a state of being engaged with the retrieval puncture needle 14 via the lock part 15. Therefore, by removing the medical suturing tool 10 out from the patient's body, the surgical suture 16 is brought into a state in which the both end portions thereof are extended out of the patient's body while joining the stomach wall B and the abdominal wall A as shown in FIG. 13. By cutting the both end portions of the projecting surgical suture 16 to a predetermined length and knotting together the end portions, a state shown in FIG. 14 is achieved, whereby suture is completed.

As described above, according to the medical suturing tool 10, the surgical suture 16 can be engaged with the retrieval puncture needle 14 via the lock part 15 only by inserting the lock part 15 including the surgical suture 16 connected thereto at a predetermined position in the insertion puncture needle 13, puncturing the insertion puncture needle 13 and the retrieval puncture needle 14 into the patient's body and performing the operation to pull the surgical suture 16 and the operation to feed the same into the insertion puncture needle 13. Then, by knotting together the end portions of the surgical suture 16 after having pulled out the insertion puncture needle 13 and the retrieval puncture needle 14, suture is completed. Therefore, the operation for suturing can be performed extremely easily.

At this time, taking over of the lock part 15 from the insertion puncture needle 13 to the retrieval puncture needle 14 can be performed smoothly. Also, the lock part 15 stored in the hole 14a of the retrieval puncture needle 14 is fixed by the engagement between the spherical portion 15a and the engaged portion 19c, and ensures connection between the surgical suture 16 and the retrieval puncture needle 14. Since the engaged portion 19c is provided in the hole 14a downwardly of the wide upper portion 19a, the lock part 15 is prevented form coming off the engaging groove 19, and hence connection between the surgical suture 16 and the retrieval puncture needle 14 is further ensured.

In this case, even in a state in which the spherical portion 15a of the lock part 15 is accommodated in the hole 14a of the retrieval puncture needle 14, and the rod-shaped portion 15b is not accommodated in the hole 14a, for example, when the lock part 15 rests in an intermediate state as shown in FIG. 11, when the insertion puncture needle 13 and the retrieval puncture needle 14 are pulled out from the body of the patient while feeding the surgical suture 16, the rod-shaped portion 15b of the lock part 15 comes into abutment with the stomach wall B of the patient, whereby the rod-shaped portion 15b enters the hole 14a of the retrieval puncture needle 14. Therefore, the lock part 15 is brought into a state shown in FIG. 12, whereby the suturing tool 10 can be pulled out without any difficulty.

In the medical suturing tool 10, the insertion puncture needle 13 and the retrieval puncture needle 14 are detachably attached to the upper retaining member 11 and the lower retaining member 12, and the mounting position can be set arbitrarily. Therefore, the length of the insertion puncture needle 13 and the retrieval puncture needle 14 projecting downwardly of the lower retaining member 12 can be adjusted to the suitable state according to the physical constitution of the patient's body or the mounting position. Since the insertion puncture needle 13 and the retrieval puncture needle 14 are attachable and detachable to the upper retaining member 11 and the lower retaining member 12, it is also possible to use the medical suturing tool 10 repeatedly, replacing one or other of the puncture needles, depending on the situation.

Second Embodiment

Figure 15:
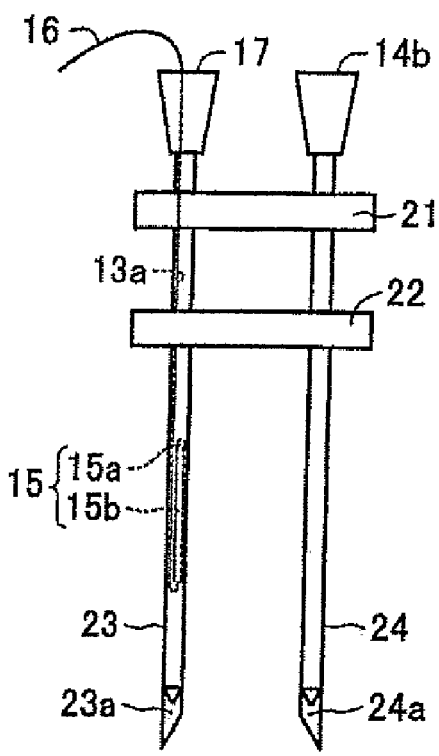
FIG. 15 is a front view showing a medical suturing tool according to a second embodiment of the present invention.
Figure 16:
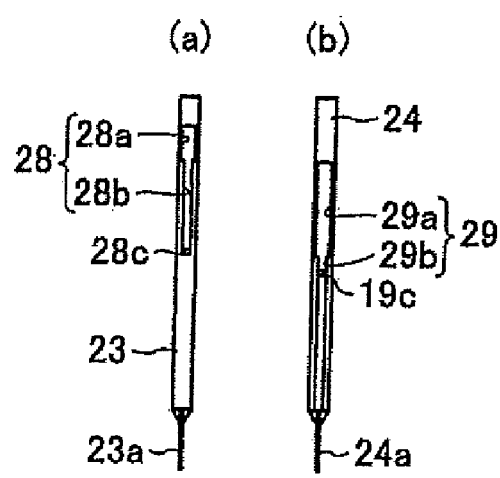
FIG. 16 shows a principal portion of the medical suturing tool shown in FIG. 15, in which (a) is a side view showing an elongate opening provided on the insertion puncture needle, and (b) is a side view showing an engaging groove provided on the retrieval puncture needle.

FIG. 15 shows a medical suturing tool 20 according to a second embodiment of the present invention. In this medical suturing tool 20, an insertion puncture needle 23 is formed into a square tubular shape, and the needle point 23a at the distal end thereof is formed like a cutting blade of a knife. In other words, a needle point 23a is formed at the lower edge portion into an inclined thin-plate shape, and the inclined lower end is formed into a sharp needlepoint. As shown in FIG. 16(a), the insertion puncture needle 23 has a vertically elongated opening 28 including a wide upper portion 28a and a narrow lower portion 28b on the side of the upper end of inclination of the needle point 23a.

A retrieval puncture needle 24 is formed into a square tubular shape, and a needle point 24a at the distal end is formed into the same shape as the needle point 23a of the insertion puncture needle 23. Then, as shown in FIG. 16(b), the retrieval puncture needle 24 has an engaging groove 29 including a wide upper portion 29a and a narrow lower portion 29b on the side of the upper end of inclination of the needle point 24a. The insertion puncture needle 23 and the retrieval puncture needle 24 are retained by an upper retaining member 21 and a lower retaining member 22. The upper retaining member 21 is formed substantially into the same shape as the upper retaining member 11, and the lower retaining member 22 is formed substantially into the same shape as the upper retaining member 12.

Retaining holes (not shown) provided on the upper retaining member 21 and the lower retaining member 22 are formed into a square shape corresponding to the shape of the insertion puncture needle 23 and the retrieval puncture needle 24 in lateral cross section. The insertion puncture needle 23 and the retrieval puncture needle 24 are retained by the upper retaining member 21 and the lower retaining member 22 in a state in which the vertically elongated opening 28 and the engaging groove 29 are opposed to each other. The other structures of the medical suturing tool 20 are the same as those of the aforementioned medical suturing tool 10. Therefore, the same parts are represented by the same reference numerals.

In this manner, in the medical suturing tool 20, since the retrieval puncture needle 24 is formed of solid portion other than the portion formed with the engaging groove 29, the void portion formed in the retrieval puncture needle 24 can be minimized, and hence the rigidity of the retrieval puncture needle 24 may be increased. The needlepoint 23a of the insertion puncture needle 23 and the needlepoint 24a of the retrieval puncture needle 24 are formed into a thin-plate shape having no hole formed thereon, the insertion puncture needle 23 and the retrieval puncture needle 24 can be punctured into an appropriate portion of the patient.

The insertion puncture needle 23 and the retrieval puncture needle 24 are formed into a shape that is square in lateral cross section, and the vertically elongated opening 28 and the engaging groove 29 are formed on the opposing sides thereof. Therefore, the direction in which the lock part 15 is bent and projects from the insertion puncture needle 23 becomes constant. Also, since the engaging groove 29 of the retrieval puncture needle 24 for receiving the lock part 15 projecting from the insertion puncture needle 23 faces the front surface of the lock part 15, taking over of the lock part 15 from the insertion puncture needle 23 and the retrieval puncture needle 24 is reliably performed.

Also, the lateral cross section of the insertion puncture needle 23 and the retrieval puncture needle 24 is formed into a square shape and the retaining holes formed on the upper retaining member 21 and the lower retaining member 22 are formed into a square shape corresponding to the lateral cross section of the insertion puncture needle 23 and the retrieval puncture needle 24. Therefore, the insertion puncture needle 23 and the retrieval puncture needle 24 are disposed so as to always be a constant relative relation. Accordingly, taking-over of the lock part 15 from the insertion puncture needle 23 to the retrieval puncture needle 24 is reliably performed. Other effects of the medical suturing tool 20 are the same as the aforementioned medical suturing tool 10.

Third Embodiment

Figure 17:
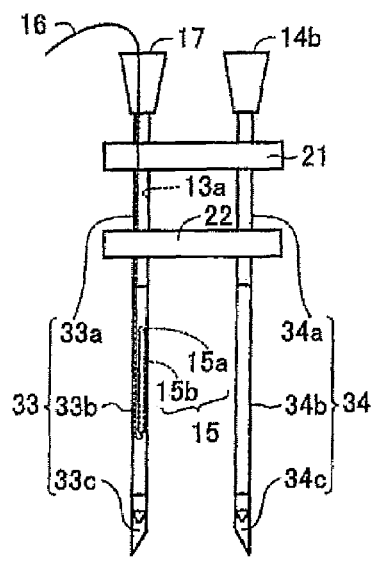
FIG. 17 is a front view showing a medical suturing tool according to a third embodiment of the present invention.

FIG. 17 shows a medical suturing tool 30 according to a third embodiment of the present invention. In this medical suturing tool 30, an insertion puncture needle 33 includes an upper insertion portion 33a, an opening-formed portion 33b, and a needle point 33c joined together. The upper insertion portion 33a and the needle point 33c are formed of metal material, and the opening-formed portion 33b is formed of mold of resin material. The entire shape of the insertion puncture needle 33 is the same as the insertion puncture needle 23.

The retrieval puncture needle 34 includes an upper portion 34a, an engaging-groove-formed portion 34b, and the needle point 34c joined together. The upper portion 34a and the needle point 34c are formed of metal material, and the engaging-groove-formed portion 34b is formed of mold of resin material. The entire shape of the retrieval puncture needle 34 is the same as the retrieval puncture needle 24. Other structures of the medical suturing tool 30 are the same as those of the aforementioned medical suturing tool 20. Therefore, the same parts are represented by the same reference numerals.

With this arrangement, in the medical suturing tool 30, molding of the opening-formed portion 33b and the engaging-groove-formed portion 34b can be performed easily with high degree of accuracy and, furthermore, the rigidity can be improved for the portions other than the opening-formed portion 33b and the engaging-groove-formed portion 34b. Other effects of the medical suturing tool 30 are the same as the aforementioned medical suturing tool 20.

Fourth Embodiment

Figure 18:
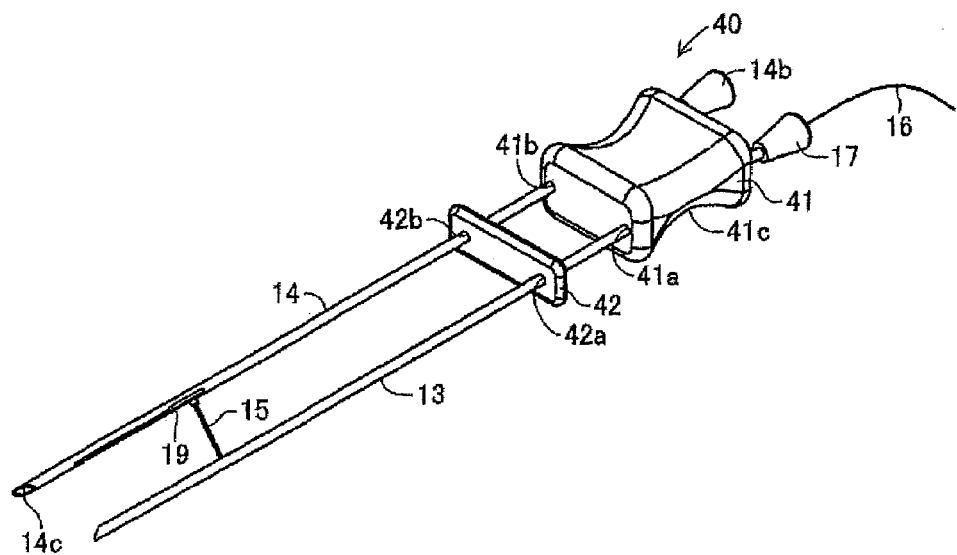
FIG. 18 is a perspective view showing a medical suturing tool according to a fourth embodiment of the present invention.
Figure 19:
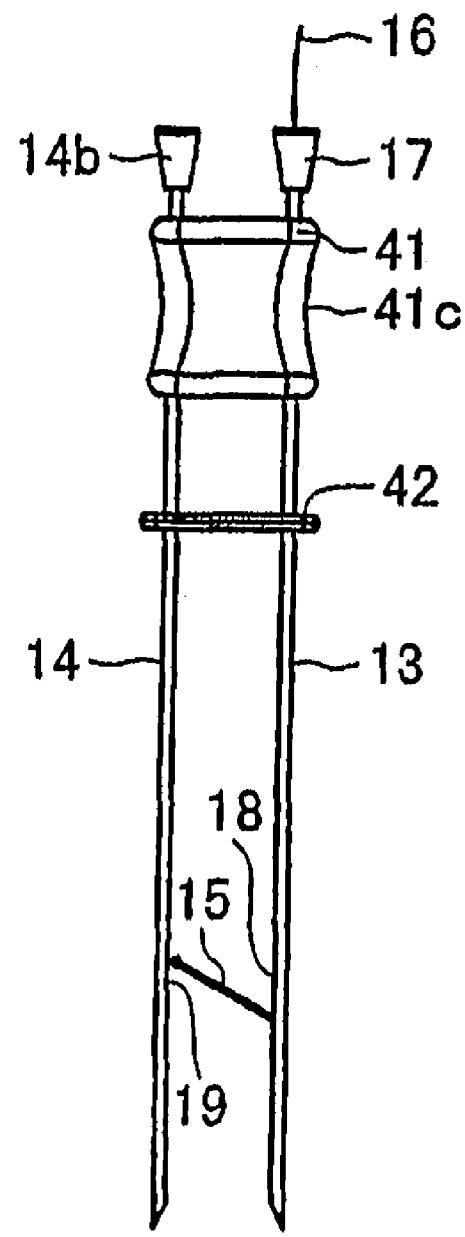
FIG. 19 is a front view of the medical suturing tool shown in FIG. 18.
Figure 20:
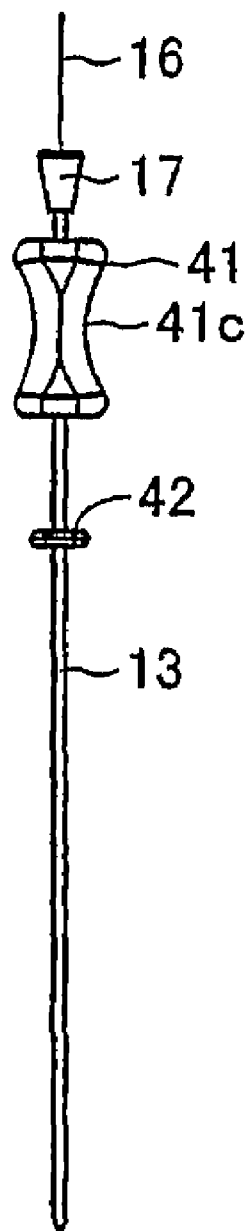
FIG. 20 is a side view of the medical suturing tool shown in FIG. 18.

FIG. 18 to FIG. 20 shows a medical suturing tool 40 according to a fourth embodiment of the invention. In this medical suturing tool 40, a lower retaining member 42 constituting the retaining member is formed into a substantially rectangular plate shape as in the case of the aforementioned lower retaining member 12, 22. However, an upper retaining member 41 is formed of a member which is substantially rectangular in cross section and elongated in the vertical direction. The respective side surfaces of the upper retaining member 41 are formed into inwardly curved surfaces, and hence a center portion 41c of the upper retaining member 41 is thinner than the upper and lower portion.

Therefore, in the medical suturing tool 40, the center portion 41c of the upper retaining member 41 can be used as a grip member for holding by hand. The upper retaining member 41 is formed with retaining holes 41a, 41b, and the lower retaining member 42 is formed with retaining holes 42a, 42b. Other portions of the medical suturing tool 40 are the same as the aforementioned medical suturing tool 10. Therefore, the same parts from FIG. 18 to FIG. 20 are represented by the same reference numerals.

With this arrangement, the medical suturing tool 40 can more easily be held by hand, and the puncturing operation can be performed more easily. Since the length of the portions of the insertion puncture needle 13 and the retrieval puncture needle 14 supported by the upper retaining member 41 increases, the strength of fixation of the insertion puncture needle 13 and the retrieval puncture needle 14 to the retaining member also increases. Accordingly, the distal portions of the insertion puncture needle 13 and the retrieval puncture needle 14 are prevented from bending or sagging in the direction away from each other during the puncturing step.

The medical suturing tool according to the present invention is not limited to the aforementioned embodiments, and may be implemented in modified modes as needed. For example, when the suturing operation is repeated for the plurality of times, a plurality of cartridges having the lock part 15 and the surgical suture 16 pushed into the insertion puncture needles 13, 23, 33 may be prepared in advance so that the operation can be repeated by replacing only the cartridge. In this way, the step of pushing the lock part 15 and the surgical suture 16 into the insertion puncture needle 23 or the like at every operation can be avoided.

It is also possible with all embodiments to form the upper retaining members 11, 21, 41 and the lower retaining members 12, 22, 42 with large members, and provide a plurality of pairs of the insertion puncture needle and the retrieval puncture needle. Accordingly, since a plurality of locations can be sutured by one operation, the operation can be performed effectively in a short time. In the respective embodiments described above, mounting of the insertion puncture needle and the retrieval puncture needle to the upper retaining member and the lower retaining member is performed by inserting the insertion puncture needle and the retrieval puncture needle into the retaining holes. However, it is also possible to form a notch on the upper retaining member to attach or detach the insertion puncture needle and the retrieval puncture needle through the notch.

Furthermore, it is also possible to provide a positioning member including a projection, a groove, or a shoulder which can engage with each other in order to make the mounting position of the insertion puncture needle and the retrieval puncture needle with respect to the upper retaining member and the lower retaining member constant. Accordingly, the insertion puncture needle and the retrieval puncture needle can be attached to the upper retaining member and the lower retaining member always at a constant relative position. Although the lateral cross sections of the insertion puncture needle and the retrieval puncture needle are circular or square in the aforementioned embodiments, they may be triangular or of other polygonal shape.

The shape of the needle point of the insertion puncture needle or the retrieval puncture needle is not limited to the shape formed by obliquely cutting the cylindrical body or the shape like the cutting blade of the knife, and may be determined freely and assume, for example, a sharp conical needle point. Although the upper end of the lock part 15 is formed with the spherical portion 15a, a disk-shaped or rod-shaped upper end portion can be employed instead. It is also contemplated to make the spherical portion 15a of the lock part 15 of heavy material and the rod-shaped portion 15b of lightweight material, and to eliminate the engaged portion 19c on the retrieval puncture needle 14, so that the lock part 15 enters the retrieval puncture needle 14 through the engaging grooves 19, 29 of the retrieval puncture needle 14 with the spherical portion 15a oriented downward.

Although the lock part 15 is employed as an engaging member in the aforementioned respective embodiments, the engaging member is not limited thereto. For example, it is also applicable to form the distal end of the surgical suture 16 into the ring shape, and form a recess or the like on the retrieval puncture needle, so that the ring-shaped portion of the surgical suture 16 is engaged with the recess or the like on the retrieval puncture needle. It is also possible to employ other engaging members which can connect the surgical suture and the retrieval puncture needle. The usefulness of the medical suturing tool of the present invention is not confined to suturing of the abdominal wall A and the stomach wall B, but may be useful also for other portions in the body.

The invention claimed is:

1. A medical suturing tool (10) comprising:
    an insertion puncture needle (13) formed with an insertion hole (13a) extending from a proximal end to a distal end thereof;
    a retrieval puncture needle (14) disposed substantially in parallel with the insertion puncture needle at a predetermined distance therefrom;
    a surgical suture (16) extending from the proximal end of the insertion puncture needle through the distal end and then engaged with the distal end of the retrieval puncture needle (14) via an engaging portion (15), wherein pulling on the suture causes the engaging portion to emerge from the insertion needle (13) and extend across to the retrieval needle (14) so that, with withdrawal of the retrieval needle (14), the suture is advanced from a puncture made by the insertion needle (13) to a puncture made by the retrieval needle (14);

an elongate opening (18) provided on a surface of the insertion puncture needle (13) opposing to the retrieval puncture needle (14) in communication with the insertion hole (13a);

an engaging member (15) being capable of moving in the insertion hole of the insertion puncture needle and, when having reached a predetermined position in the insertion hole, bending from the side of the upper end portion thereof to project outside from the elongate opening; and an engaging groove (19) provided on a surface of the retrieval puncture needle (14) opposing to the insertion puncture needle (13), wherein the surgical suture (16) is connected to the lower end of the engaging member so that the suturing tool engages with the engaging groove on the retrieval puncture needle after having passed from the proximal end to the distal end of the insertion puncture needle together with the engaging member;

wherein the upper end portion (15a) of the engaging member is thicker than the lower side portion 15b of the engaging member, the elongate opening of the insertion puncture needle (13) including a wide upper portion (18a) through which the upper end portion of the engaging member can pass and a narrow lower portion (18b) through which the upper end portion of the engaging member cannot pass and the lower side portion of the engaging member can pass, and the engaging groove of the retrieval puncture needle (14) including a wide upper portion (19a) through which the upper end portion of the engaging member can enter and a narrow lower portion (19) through which the upper end portion of the engaging member cannot pass but the lower side portion can enter.

2. A tool according to claim 1 wherein the engaging groove (19) includes a storage recess capable of accommodating the engaging member (15) and an engaged portion (19c) with which the upper end portion of the engaging member can engage.

3. A tool according to claim 1, wherein the upper end portion (15a) of the engaging member comprises a spherical body and the lower side portion (15b) of the engaging member comprises a rod member having smaller diameter than the spherical body.

4. A tool according to claim 1, wherein an engaging wall is provided at the lower portion of the surface of the wide upper portion of the engaging groove of the retrieval puncture needle (14) so that the upper end portion of the engaging member is prevented from coming off toward the outside from the wide upper portion of the engaging groove.

5. A tool according to claim 1, wherein the portion on the distal side of the insertion puncture needle (13) with respect to the elongate opening and at least part of the retrieval puncture needle (14), other than the portion where the engaging groove is formed, is formed as a solid portion.

6. A tool according to claim 1, wherein at least a portion of the insertion puncture needle (13) where the elongate opening is formed and at least a portion of the retrieval puncture needle (14) where the engaging groove is formed are formed into an angular C-shape in lateral cross section, respectively, and are arranged so that the open sides are opposed to each other.

7. A tool according to claim 1, wherein needle points of the insertion puncture needle (13) and the retrieval puncture needle (14) are formed into a pointed conical shape or a tapered thin blade shape.

8. A tool according to claim 1, wherein at least one of the insertion puncture needle (13) and the retrieval puncture needle (14) is formed by connecting a metal member and a resin member.

9. A tool according to claim 1, wherein the insertion puncture needle (13) and the retrieval puncture needle (14) are releasably attached to a retaining member (11, 12, 41).

10. A tool according to claim 9, wherein the retaining member is constituted of a grip member (41) to be held by a hand.

11. A tool according to claim 9, wherein a plurality of pairs of the insertion puncture needle (13) and the retrieval puncture needle (14) are provided on the retaining member.

* * * * *

UNITED STATES PATENT AND TRADEMARK OFFICE
CERTIFICATE OF CORRECTION

PATENT NO. : 7,625,386 B2 Page 1 of 1
APPLICATION NO. : 10/598561
DATED : December 1, 2009
INVENTOR(S) : Abe et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 158 days.

Signed and Sealed this

Twenty-sixth Day of October, 2010

David J. Kappos
*Director of the United States Patent and Trademark Office*